(12) United States Patent
Northrop et al.

(10) Patent No.: US 11,090,604 B2
(45) Date of Patent: Aug. 17, 2021

(54) ENHANCED ACID GAS REMOVAL WITHIN A GAS PROCESSING SYSTEM

(71) Applicant: ExxonMobil Upstream Research Company

(72) Inventors: P. Scott Northrop, Spring, TX (US); J. Timothy Cullinane, Montgomery, TX (US)

(73) Assignee: ExxonMobil Upstream Research Company, Spring, TX (US)

( * ) Notice: Subject to any disclaimer, the term of this patent is extended or adjusted under 35 U.S.C. 154(b) by 0 days.

(21) Appl. No.: 16/660,184

(22) Filed: Oct. 22, 2019

(65) Prior Publication Data

US 2021/0113956 A1 Apr. 22, 2021

Related U.S. Application Data

(60) Provisional application No. 62/769,144, filed on Nov. 19, 2018.

(51) Int. Cl.
  *B01D 53/14* (2006.01)
  *B01D 53/40* (2006.01)
  (Continued)

(52) U.S. Cl.
  CPC ......... *B01D 53/18* (2013.01); *B01D 53/1406* (2013.01); *B01D 53/1462* (2013.01);
  (Continued)

(58) Field of Classification Search
  None
  See application file for complete search history.

(56) References Cited

U.S. PATENT DOCUMENTS 5,622,681 A 4/1997 Grierson et al.
7,377,967 B2 5/2008 Reddy et al.
(Continued)

FOREIGN PATENT DOCUMENTS

WO 2018/164705 9/2018

OTHER PUBLICATIONS

Rolker, J. et al. (2011) "Industrial Progress: New Energy-Efficient Adsorbents for the CO2 Separation From Natural Gas, Syngas and Flue Gas," Advances in Chemical Engineering and Science, pp. 280-288.

*Primary Examiner* — Daniel Berns
(74) *Attorney, Agent, or Firm* — ExxonMobil Upstream Research Company—Law Department

(57) ABSTRACT

A gas processing system is described herein. The gas processing system includes a number of co-current contacting systems configured to contact a sour feed gas stream including an acid gas with a solvent stream to produce a partially-sweetened gas stream and a rich solvent stream including an absorbed acid gas. At least one of the co-current contacting systems is configured to send the rich solvent stream to a regenerator. The regenerator is configured to remove the absorbed acid gas from the rich solvent stream to produce a lean solvent stream. The gas processing system also includes a solvent treater configured to treat at least a portion of the lean solvent stream to produce an enhanced solvent stream, and a final co-current contacting system configured to contact the partially-sweetened gas stream with the enhanced solvent stream to produce a partially-loaded solvent stream and a final gas stream.

7 Claims, 7 Drawing Sheets

(51) Int. Cl.
  *B01D 53/78* (2006.01)
  *B01D 53/96* (2006.01)
  *B01D 53/18* (2006.01)
  *G01N 33/00* (2006.01)

(52) U.S. Cl.
  CPC ..... *B01D 53/1468* (2013.01); *B01D 53/1475* (2013.01); *G01N 33/0036* (2013.01)

(56) References Cited

U.S. PATENT DOCUMENTS

| | | |
|---|---|---|
| 8,899,557 B2 | 12/2014 | Cullinane et al. |
| 10,130,897 B2 | 11/2018 | Grave et al. |
| 10,155,193 B2 | 12/2018 | Cullinane et al. |
| 10,293,299 B2 | 5/2019 | Laroche et al. |
| 10,300,429 B2 | 5/2019 | Grave et al. |
| 10,343,107 B2 | 7/2019 | Northrop et al. |
| 10,391,442 B2 | 8/2019 | Freeman et al. |
| 10,561,976 B2 | 2/2020 | Yoon et al. |
| 2017/0157553 A1* | 6/2017 | Northrop ................ C10L 3/104 |

* cited by examiner

200

600

ENHANCED ACID GAS REMOVAL WITHIN A GAS PROCESSING SYSTEM

CROSS REFERENCE TO RELATED APPLICATION

This application claims the priority benefit of U.S. Provisional Patent Application No. 62/769,144 filed Nov. 19, 2018, entitled ENHANCED ACID GAS REMOVAL WITHIN A GAS PROCESSING SYSTEM.

FIELD

The present techniques provide for the enhanced removal of acid gas from a gas stream using treated solvent within a gas processing system including a co-current flow scheme. More specifically, the present techniques provide for the use of a solvent treater in connection with the final stage of the gas processing system to enhance the solvent's ability to selectively remove acid gas from the gas stream.

BACKGROUND

This section is intended to introduce various aspects of the art, which may be associated with exemplary embodiments of the present techniques. This discussion is believed to assist in providing a framework to facilitate a better understanding of particular aspects of the present techniques. Accordingly, it should be understood that this section should be read in this light, and not necessarily as admissions of prior art.

The production of hydrocarbons from a reservoir oftentimes carries with it the incidental production of non-hydrocarbon gases. Such gases include contaminants such as hydrogen sulfide ($H_2S$) and carbon dioxide ($CO_2$). When $H_2S$ and $CO_2$ are produced as part of a hydrocarbon gas stream, the raw gas stream is sometimes referred to as "sour gas." The $H_2S$ and $CO_2$ are often referred to together as "acid gases."

In addition to hydrocarbon production streams, acid gases may be associated with synthesis gas streams, or with refinery gas streams. Acid gases may also be present within so-called flash-gas streams in gas processing facilities. Further, acid gases may be generated by the combustion of coal, natural gas, or other carbonaceous fuels.

Natural gas streams may contain not only $H_2S$ and $CO_2$, but may also contain other "acidic" impurities. These include mercaptans and other trace sulfur compounds (e.g., COS). In addition, natural gas streams may contain water. Such impurities are often removed prior to industrial or residential use. For example, natural gas streams are typically purified to concentrations of less than 4 parts per million (ppm) $H_2S$ and less than 2-3 volume percent (vol. %) $CO_2$ prior to sale. The extent to which such impurities must be removed is dictated by pipeline regulations, which help to ensure public safety and maintain the integrity of the pipeline by reducing corrosion.

Acid gas removal is an expensive and equipment-intensive process. The removal of $H_2S$ from natural gas streams is especially complicated due to the safety, health, and environmental considerations when working with toxic $H_2S$ and the processing of sulfur by-products into solid sulfur, or the injection of $H_2S$-rich gas through acid gas injection methods.

Various processes have been devised to remove acid gases from a raw natural gas stream. For example, the raw natural gas stream may be treated with a solvent. Solvents may include chemical solvents such as amines. Examples of amines used in sour gas treatment include monoethanol amine (MEA), diethanol amine (DEA), and methyl diethanol amine (MDEA).

Physical solvents are sometimes used in lieu of chemical solvents. Examples include SELEXOL™ (available from Dow Chemical Company) and RECTISOL® (available from The Linde Group). However, chemical solvents are generally more effective than physical solvents, particularly at feed gas pressures below about 300 psia (2.07 MPa). In some instances, hybrid solvents, meaning mixtures of physical and chemical solvents, have been used. An example is Sulfinol®.

Chemical solvents, such as amine-based solvents, rely on a chemical reaction between the solvent and the acid gases within the natural gas stream. The reaction process is sometimes referred to as "gas sweetening." As an example, the reactions of acid gases with tertiary amines ($R_1R_2R_3$—N) are shown below in Eq. 1 and 2.

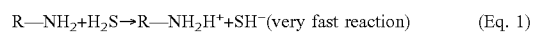
$$R-NH_2 + H_2S \rightarrow R-NH_2H^+ + SH^- \text{ (very fast reaction)} \quad \text{(Eq. 1)}$$

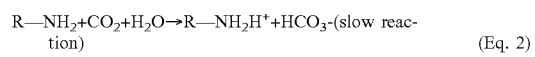
$$R-NH_2 + CO_2 + H_2O \rightarrow R-NH_2H^+ + HCO_3^- \text{ (slow reaction)} \quad \text{(Eq. 2)}$$

As shown in Eq. 1, the reaction of $H_2S$ with the amine is inherently very fast and is often considered instantaneous with respect to diffusion and other kinetic limitations. However, as shown in Eq. 2, the reaction of $CO_2$ is somewhat slower. The difference in these reaction rates can be utilized to selectively remove one impurity over another within a gas processing system. Note that primary and secondary amines offer a faster reaction route with $CO_2$ to form carbamates. Consequently, those amines normally cannot be used for selective $H_2S$ removal. Exceptions to this include "sterically-hindered" amines, which prevent the $CO_2$ from reacting with the amino hydrogen to form carbamates.

Shale gas often requires $H_2S$ removal with little to no $CO_2$ removal. Therefore, selective $H_2S$ removal is becoming a central part of the processing facility for natural gas assets. To accomplish this, a solvent with a high selectivity for $H_2S$ may be used. The "$H_2S$ selectivity" of the solvent is defined as the ratio of $H_2S$ removal to $CO_2$ removal, which is a function of the respective reaction rates. A high $H_2S$ selectivity may be obtained by using solvents that have a slower reaction rate with $CO_2$. Similarly, the contact time of the gas and liquid phases can be minimized to enhance $H_2S$ uptake over $CO_2$.

SUMMARY

An exemplary embodiment provides a gas processing system. The gas processing system includes a number of co-current contacting systems configured to contact a sour feed gas stream including acid gas with a solvent stream to produce a partially-sweetened gas stream and a rich solvent stream including absorbed acid gas. At least one of the co-current contacting systems is configured to send the rich solvent stream to a regenerator. The regenerator is configured to remove the absorbed acid gas from the rich solvent stream to produce a lean solvent stream. The gas processing system also includes a solvent treater configured to treat at least a portion of the lean solvent stream to produce an enhanced solvent stream, and a final co-current contacting system configured to contact the partially-sweetened gas stream with the enhanced solvent stream to produce a partially-loaded solvent stream and a final gas stream.

Another exemplary embodiment provides a method for enhanced acid gas removal within a gas processing system.

The method includes contacting a sour feed gas stream including acid gas with a solvent stream within a number of co-current contacting systems to produce a partially-sweetened gas stream and a rich solvent stream including absorbed acid gas. The method also includes removing the absorbed acid gas from the rich solvent stream within a regenerator to produce a lean solvent stream, and treating at least a portion of the lean solvent stream within a solvent treater to produce an enhanced solvent stream. The method further includes contacting the partially-sweetened gas stream with the enhanced solvent stream within a final co-current contacting system to produce a partially-loaded solvent stream and a final gas stream.

Another exemplary embodiment provides a gas processing system. The gas processing system includes a number of co-current contacting systems configured to contact a sour feed gas stream including acid gas with a solvent stream to produce a partially-sweetened gas stream and a rich solvent stream including a first portion of the acid gas. The gas processing system includes a first regenerator configured to remove the first portion of the acid gas from the rich solvent stream to regenerate the solvent stream, and recirculate the solvent stream into at least one of the co-current contacting systems. The gas processing system also includes a final co-current contacting system configured to contact the partially-sweetened gas stream with an enhanced solvent stream to produce a final gas stream and a partially-loaded solvent stream including a second portion of the acid gas. The gas processing system further includes a second regenerator configured to remove the second portion of the acid gas from the partially-loaded solvent stream to produce a lean solvent stream, and a solvent treater configured to treat at least a portion of the lean solvent stream to produce the enhanced solvent stream that is contacted with the partially-sweetened gas stream within the final co-current contacting system.

DESCRIPTION OF THE DRAWINGS

The advantages of the present techniques are better understood by referring to the following detailed description and the attached drawings, in which.

DETAILED DESCRIPTION

Figure 1A:
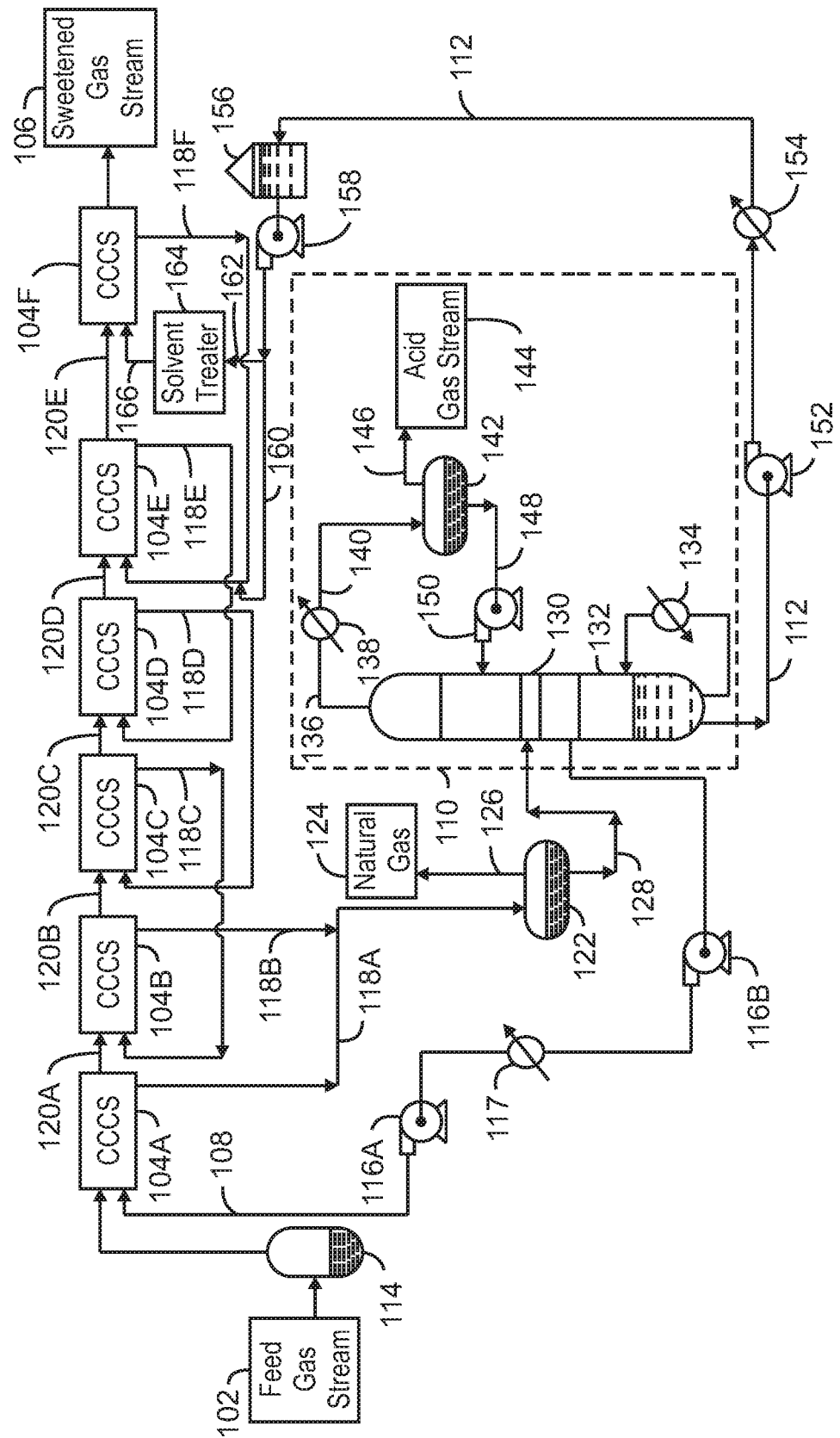
FIG. 1A is a process flow diagram of a gas processing system that includes a co-current flow scheme and is configured for enhanced acid gas removal.

In the following detailed description section, specific embodiments of the present techniques are described. However, to the extent that the following description is specific to a particular embodiment or a particular use of the present techniques, this is intended to be for exemplary purposes only and simply provides a description of the exemplary embodiments. Accordingly, the techniques are not limited to the specific embodiments described below, but rather, include all alternatives, modifications, and equivalents falling within the true spirit and scope of the appended claims.

At the outset, for ease of reference, certain terms used in this application and their meanings as used in this context are set forth. To the extent a term used herein is not defined below, it should be given the broadest definition persons in the pertinent art have given that term as reflected in at least one printed publication or issued patent. Further, the present techniques are not limited by the usage of the terms shown below, as all equivalents, synonyms, new developments, and terms or techniques that serve the same or a similar purpose are considered to be within the scope of the present claims.

"Acid gas" refers to any gas that dissolves in water, producing an acidic solution. Non-limiting examples of acid gases include hydrogen sulfide ($H_2S$), carbon dioxide ($CO_2$), sulfur dioxide ($SO_2$), carbon disulfide ($CS_2$), carbonyl sulfide (COS), mercaptans, or mixtures thereof.

"Co-current contactor" refers to a vessel that receives a stream of gas and a separate stream of solvent in such a manner that the gas stream and the solvent stream contact one another while flowing in generally the same directions within the contactor.

The term "co-currently" refers to the internal arrangement of process streams within a unit operation that can be divided into several sub-sections by which the process streams flow in the same direction.

The term "dehydrated natural gas stream" refers to a natural gas stream that has undergone a dehydration process. Typically, the dehydrated natural gas stream has a water content of less than 7 lb $H_2O$/million standard cubic feet for US pipeline applications, or less than 0.1 ppm for LNG applications. Any suitable process for dehydrating the natural gas stream can be used. Typical examples of suitable dehydration processes include, but are not limited to, treatment of the natural gas stream with molecular sieves (for LNG specifications) or dehydration using glycol or methanol (for U.S. pipeline specifications). Alternatively, the natural gas stream can be dehydrated by formation of methane hydrates; for example, using a dehydration process as described in WO 2004/070297.

As used herein, the term "dehydration" refers to the pre-treatment of a raw feed gas stream to obtain a dehydrated natural gas stream by partially or completely removing water and, optionally, some heavy hydrocarbons from the feed gas stream. This can be accomplished by means of a pre-cooling cycle, against an external cooling loop or a cold internal process stream, for example. Water may also be removed by means of pre-treatment with molecular sieves, e.g. zeolites, or silica gel or alumina oxide or other drying agents. Water may also be removed by means of washing with glycol, monoethylene glycol (MEG), diethylene glycol (DEG) or triethylene glycol (TEG), or glycerol. The amount of water in the gas feed stream is suitably less than 1 volume percent (vol. %), preferably less than 0.1 vol. %, more preferably less than 0.01 vol. %.

As used herein, the term "fluid" refers to gases, liquids, and combinations of gases and liquids, as well as to combinations of gases and solids, and combinations of liquids and solids.

The term "flue gas" refers to any gas stream generated as a by-product of hydrocarbon combustion.

The term "gas" is used interchangeably with "vapor," and is defined as a substance or mixture of substances in the gaseous state as distinguished from the liquid or solid state. Likewise, the term "liquid" means a substance or mixture of substances in the liquid state as distinguished from the gas or solid state.

A "hydrocarbon" is an organic compound that primarily includes the elements hydrogen and carbon, although nitrogen, sulfur, oxygen, metals, or any number of other elements may be present in small amounts. As used herein, the term "hydrocarbon" generally refers to components found in natural gas, oil, or chemical processing facilities. Moreover, the term "hydrocarbon" may refer to components found in raw natural gas, such as $CH_4$, $C_2H_6$, $C_3$ isomers, $C_4$ isomers, benzene, and the like.

With respect to fluid processing equipment, the term "in series" means that two or more devices are placed along a flow line such that a fluid stream undergoing fluid separation moves from one item of equipment to the next while maintaining flow in a substantially constant downstream direction. Similarly, the term "in line" means that two or more components of a fluid mixing and separating device are connected sequentially or, more preferably, are integrated into a single tubular device.

The term "industrial plant" refers to any plant that generates a gas stream containing at least one hydrocarbon or an acid gas. One non-limiting example is a coal-powered electrical generation plant. Another example is a cement plant that emits $CO_2$ at low pressures.

The term "liquid solvent" refers to a fluid in substantially liquid phase that preferentially absorbs one component over another. For example, a liquid solvent may preferentially absorb an acid gas, thereby removing or "scrubbing" at least a portion of the acid gas component from a gas stream. Moreover, a liquid solvent may preferentially absorb one acid gas over another.

"Natural gas" refers to a multi-component gas obtained from a crude oil well or from a subterranean gas-bearing formation. The composition and pressure of natural gas can vary significantly. A typical natural gas stream contains methane ($CH_4$) as a major component, i.e., greater than 50 mole percent (mol. %) of the natural gas stream. The natural gas stream can also contain ethane ($C_2H_6$), higher molecular weight hydrocarbons (e.g., $C_3$-$C_{20}$ hydrocarbons), acid gases (e.g., carbon dioxide and hydrogen sulfide), or any combinations thereof. The natural gas can also contain minor amounts of contaminants such as water, nitrogen, iron sulfide, wax, crude oil, or any combinations thereof. The natural gas stream may be substantially purified prior to use in embodiments described herein, so as to remove compounds that may act as poisons.

"Non-absorbing gas" means a gas that is not significantly absorbed by a solvent during a gas treating or conditioning process.

As used herein, "purification" includes separation processes by which impurities that may cause problems to downstream processes are removed.

"Solvent" refers to a substance capable at least in part of dissolving or dispersing other substances, such as to provide or form a solution. The solvent may be polar, nonpolar, neutral, protic, aprotic, or the like. The solvent may include any suitable element, molecule, or compound, such as methanol, ethanol, propanol, glycols, ethers, ketones, other alcohols, amines, salt solutions, or the like. The solvent may include physical solvents, chemical solvents, or the like. The solvent may operate by any suitable mechanism, such as physical absorption, chemical absorption, chemisorption, physisorption, adsorption, pressure swing adsorption, temperature swing adsorption, or the like. Specific solvents that are useful for acid gas absorption include, but are not limited to, monoethanolamine (MEA), 2(2-aminoethoxy) ethanol [Diglycolamine® (DGA)], diethanolamine (DEA), diisopropanolamine (DIPA), methyldiethanolamine (MDEA), triethyleneamine, FLEXSORB® SE, 2-amino-2-methyl-1-propanol (AMP), or formulated amines such as FLEXSORB® SE PLUS, the UCARSOL™ family of products, or formulated MDEA solutions.

"Substantial" when used in reference to a quantity or amount of a material, or a specific characteristic thereof, refers to an amount that is sufficient to provide an effect that the material or characteristic was intended to provide. The exact degree of deviation allowable may depend, in some cases, on the specific context.

The term "sweetened natural gas stream" refers to a natural gas stream that has had at least a portion of acid gas components removed.

Overview

The present techniques provide for the enhanced removal of acid gas from a sour gas stream using treated solvent within a gas processing system including a co-current flow scheme. In various embodiments, the present techniques are used to selectively remove $H_2S$ from a sour natural gas stream. Specifically, the sour natural gas stream may be purified to a concentration of less than 4 ppm $H_2S$ to meet pipeline regulations.

The co-current flow scheme may utilize any number of co-current contacting systems connected in series within a pipe. A natural gas stream and a liquid solvent stream move together, i.e., co-currently, within the co-current contacting systems. In some embodiments, the natural gas stream and the liquid solvent stream move together generally along the longitudinal axis of the co-current contacting system.

Each co-current contacting system within the gas processing system may include a co-current contactor that facilitates the absorption of acid gas, such as $H_2S$ and $CO_2$, into the solvent stream. In addition, each co-current contacting system may include a separator that is capable of separating the natural gas stream from the solvent stream with the absorbed acid gas, producing a sweetened, liquid-free natural gas stream.

In some embodiments, the solvent stream is an amine-based solvent that is capable of absorbing acid gases, such as $H_2S$ and $CO_2$, within the natural gas stream. For example, the solvent may include, but is not limited to, monoethanolamine (MEA), 2(2-aminoethoxy) ethanol [Diglycolamine® (DGA)], diethanolamine (DEA), diisopropanolamine (DIPA), methyldiethanolamine (MDEA), triethyleneamine, FLEXSORB® SE, 2-amino-2-methyl-1-propanol (AMP), or formulated amines such as FLEXSORB® SE PLUS, the UCARSOL™ family of products, or formulated MDEA solutions.

According to current techniques, as the solvent flows through the series of co-current contacting systems, the solvent becomes loaded with contaminants, such as $H_2S$ and $CO_2$. For rapidly-reacting components like $H_2S$, this can result in a pinch condition near the outlet of the co-current contacting systems as the $CO_2$, which is thermodynamically favored for absorption, begins to displace the $H_2S$. For a typical shale gas application, in which it is desirable to remove up to 1,000 ppm $H_2S$, three or four co-current contacting systems may be used. However, it can be particularly challenging to reach a 4 ppm $H_2S$ specification in the final stage because the solvent will load with $H_2S$ and $CO_2$ as it flows through the device, thus reducing its capacity to further reduce the $H_2S$ concentration of the natural gas stream.

Therefore, according to embodiments described herein, enhanced $H_2S$ removal is achieved through the use of a solvent treater upstream of the final co-current contacting system. The solvent treater is configured to modify the solvent stream for increased $H_2S$ absorption in the final co-current contacting system, as described further with respect to FIGS. 1A, 1B, 2, 3, 4, and 6.

Gas Processing System

FIG. 1A is a process flow diagram of a gas processing system 100 that includes a co-current flow scheme and is configured for enhanced acid gas removal. The gas processing system 100 may be used for the removal of acid gas components, such as $H_2S$ and $CO_2$, from a feed gas stream 102. In addition, the gas processing system 100 may be used for the removal of water or other impurities from the feed gas stream 102. The gas processing system 100 may employ a number of co-current contacting systems 104A-F. Each co-current contacting system 104A-F may include a co-current contactor and a separator, for example, as discussed further with respect to FIG. 5.

The feed gas stream 102 may be, for example, a natural gas stream from a hydrocarbon production operation, a flue gas stream from a power plant, or a synthesis gas (syn-gas) stream. If the feed gas stream 102 is a syn-gas stream, the feed gas stream 102 may be cooled and filtered before being introduced into the gas processing system 100. The feed gas stream 102 may also be a flash gas stream taken from a flash drum in a gas processing facility itself. In addition, the feed gas stream 102 may be a tail gas stream from a Claus sulfur recovery process or an impurities stream from a solvent regenerator. Furthermore, the feed gas stream 102 may be an exhaust emission from a cement plant or other industrial plant. In this instance, $CO_2$ may be absorbed from excess air or from a nitrogen-containing flue gas.

The feed gas stream 102 may include a non-absorbing gas, such as methane, and one or more impurities, such as $CO_2$ and $H_2S$. In some embodiments, the feed gas stream 102 includes a large amount of $H_2S$, such as, for example, on the order of 1,000 ppm $H_2S$. The gas processing system 100 may convert the feed gas stream 102 into a sweetened gas stream 106 by removing the $CO_2$ and $H_2S$. In various embodiments, the sweetened gas stream 106 contains concentrations of less than 4 ppm $H_2S$ and less than 2-3 vol. % $CO_2$.

In operation, the feed gas stream 102 may be flowed into a first co-current contacting system 104A, where it is mixed with a solvent stream 108. In various embodiments, the solvent stream 108 includes an amine solution, such as monoethanol amine (MEA), diethanol amine (DEA), or methyldiethanol amine (MDEA). The solvent stream 108 may include a lean solvent that has undergone a desorption process for the removal of acid gas impurities. For example, in the gas processing system 100 shown in FIG. 1A, the solvent stream 108 introduced into the first co-current contacting system 104A includes a semi-lean solvent that is taken from a central portion of a regenerator 110. A lean solvent stream 112 taken from the regenerator 110 may also be directed into the fifth and final co-current contacting systems 104E and 104F.

In various embodiments, the gas processing system 100 employs a series of co-current contacting systems 104A-F. Each co-current contacting system 104A-F removes a portion of the acid gas content from the feed gas stream 102, thereby releasing a progressively sweetened gas stream in a downstream direction. The final co-current contacting system 104F provides the final sweetened gas stream 106.

Before entering the first co-current contacting system 104A, the feed gas stream 102 may pass through an inlet separator 114. The inlet separator 114 may be used to clean the feed gas stream 102 by filtering out impurities, such as brine and drilling fluids. Some particle filtration may also take place. The cleaning of the feed gas stream 102 can prevent foaming of solvent during the acid gas treatment process.

In some embodiments, the feed gas stream 102 may also be pretreated upstream of the inlet separator 114 or the first co-current contacting system 104A. For example, the feed gas stream 102 may undergo a water wash to remove glycol or other chemical additives. This may be accomplished via a separate processing loop (not shown) wherein water is introduced to the gas, such as via an additional co-current contacting system. Water has an affinity for glycol and will pull the glycol out of the feed gas stream 102. This, in turn, will help control foaming within the co-current contacting systems 104A-F. In the case of flue gas applications, corrosion inhibitors may be added to the solvent to retard the reaction of $O_2$ with the steel in the processes.

As shown in FIG. 1A, the solvent stream 108 is flowed into the first co-current contacting system 104A. Movement of the semi-lean solvent stream 108 into the first co-current contacting system 104A may be aided by pumps 116A and 116B and a cooler 117. The cooler 117 may cause the solvent stream 108 to flow into the first co-current contacting system 104A at a suitable temperature, while the pumps 116A and 116B may cause the solvent stream 108 to flow into the first co-current contacting system 104A at a suitable pressure of, for example, about 15 psia to about 1,500 psig.

Once inside the first co-current contacting system 104A, the feed gas stream 102 and the solvent stream 108 move along the longitudinal axis of the first co-current contacting system 104A. As they travel, the liquid amine (or other treating solution) interacts with the $H_2S$ and $CO_2$ in the feed gas stream 102, causing the $H_2S$ and $CO_2$ to chemically attach to or be absorbed by the amine molecules. A first partially-loaded, or "rich," solvent stream 118A may be flowed out of a bottom portion of the first co-current contacting system 104A. In addition, a first partially-sweetened gas stream 120A may be flowed out of a top portion of the first co-current contacting system 104A and into a second co-current contacting system 104B.

As shown in the example illustrated in FIG. 1A, a third co-current contacting system 104C may be provided after the second co-current contacting system 104B, and a fourth co-current contacting system 104D may be provided after the third co-current contacting system 104C. In addition, a fifth co-current contacting system 104E may be provided after the fourth co-current contacting system 104D, and a final co-current contacting system 104F may be provided after the fifth co-current contacting system 104E. Each of the second, third, fourth, and fifth co-current contacting systems 104B, 104C, 104D, and 104E may generate a respective partially-sweetened gas stream 120B, 120C, 120D, and 120E. In addition, each of the second, third, fourth, fifth, and final co-current contacting systems 104B, 104C, 104D, 104E, and 104F may generate a respective partially-loaded solvent stream 118B, 118C, 118D, 118E, and 118F. If an amine is used as the solvent stream 108, the partially-loaded solvent streams 118A-F may include rich amine solutions. In the gas processing system 100, the second partially-loaded solvent stream 118B merges with the first partially-loaded solvent stream 118A and goes through a regeneration process in the regenerator 110.

As the progressively-sweetened gas streams 120A-E are generated, the gas pressure in the gas processing system 100 will progressively decrease. As this occurs, the liquid pressure of the progressively-richer solvent streams 118A-F may be correspondingly increased. This may be accomplished by placing one or more booster pumps (not shown) between each co-current contacting system 104A-F to boost liquid pressure in the gas processing system 100.

In the gas processing system 100, solvent streams may be regenerated by flowing the partially-loaded solvent streams 118A and 118B through a flash drum 122. Absorbed natural gas 124 may be flashed from the partially-loaded solvent streams 118A and 118B within the flash drum 122, and may be flowed out of the flash drum 122 via an overhead line 126.

The resulting rich solvent stream 128 may be flowed from the flash drum 122 to the regenerator 110. The rich solvent stream 128 may be introduced into the regenerator 110 for desorption. The regenerator 110 may include a stripper portion 130 including trays or other internals (not shown). The stripper portion 130 may be located directly above a reboiler portion 132. A heat source 134 may be provided with the reboiler portion 132 to generate heat. The regenerator 110 produces the regenerated, lean solvent stream 112 that is recycled for re-use in the fifth and final co-current contacting systems 104E and 104F. Stripped overhead gas from the regenerator 110, which may include concentrated $H_2S$ and $002$, may be flowed out of the regenerator 110 as an overhead impurities stream 136.

The overhead impurities stream 136 may be flowed into a condenser 138, which may cool the overhead impurities stream 136. The resulting cooled impurities stream 140 may be flowed through a reflux accumulator 142. The reflux accumulator 142 may separate any remaining liquid, such as condensed water, from the impurities stream 140. This may result in the generation of a substantially pure acid gas stream 144, which may be flowed out of the reflux accumulator 142 via an overhead line 146.

In some embodiments, the $H_2S$ in the acid gas stream 144 is then converted into elemental sulfur using a sulfur recovery unit (not shown). The sulfur recovery unit may be a so-called Claus unit. Those of ordinary skill in the art will understand that a "Claus process" is a process that is sometimes used by the natural gas and refinery industries to recover elemental sulfur from $H_2S$-containing gas streams.

In practice, the "tail gas" from the Claus process, which may include $H_2S$, $SO_2$, $CO_2$, $N_2$, and water vapor, can be reacted to convert the $SO_2$ to $H_2S$ via hydrogenation. The hydrogenated tail gas stream has a high partial pressure, a large amount of $CO_2$, e.g., more than 50%, and a small amount of $H_2S$, e.g., a few percent or less. This type of gas stream, which is typically near atmospheric pressure, is amenable to selective $H_2S$ removal. The recovered $H_2S$ may be recycled to the front of the Claus unit, or may be sequestered downstream. Alternatively, a direct oxidation of the $H_2S$ to elemental sulfur may be performed using various processes known in the field of gas separation.

Because the $H_2S$ reaction is instantaneous relative to the $CO_2$ reactions, lowering the residence time, i.e., the contact time between the vapor and liquid phases, will result in less $CO_2$ being absorbed into the solvent. The design of the co-current contacting systems 104A-F enhances selective $H_2S$ removal due to the short contact time inherent in the equipment design.

As shown in FIG. 1A, a residual liquid stream 148 may be flowed out of the bottom of the reflux accumulator 142. The residual liquid stream 148 may be flowed through a reflux pump 150, which may boost the pressure of the residual liquid stream 148 and pump the residual liquid stream 148 into the regenerator 110. The residual liquid stream 148 may be flowed out of the regenerator 110, for example, from the bottom of the reboiler portion 132 as part of the lean solvent stream 112. Some water may be added to the lean solvent stream 112 to balance the loss of water vapor to the sweetened gas stream 106 and the acid gas stream 144. This water may be added at an intake or suction of the reflux pump 150.

The lean solvent stream 112 may be at a low pressure. Accordingly, the lean solvent stream 112 may be passed through a pressure boosting pump 152. From the pressure boosting pump 152, the lean solvent stream 112 may be flowed through a cooler 154. The cooler 154 may cool the lean solvent stream 112 back to near ambient temperatures after it has been heated by the regenerator 110.

In some embodiments, the lean solvent stream 112 may then be flowed into a solvent tank 156. In other embodiments, the solvent tank 156 is off-line and provides a reservoir for the lean solvent stream 112.

Movement of the lean solvent stream 112 towards the fifth and final co-current contacting systems 104E and 104F may be aided by a pump 158. The pump 158 may cause the lean solvent stream 112 to flow at a suitable pressure, for example, of about 15 psia to about 1,500 psig.

A first portion 160 of the lean solvent stream 112 may be joined with the partially-loaded solvent stream 118F and flowed into the fifth co-current contacting system 104E. A second portion 162 of the lean solvent stream 112 may be flowed into a solvent treater 164, which is configured to treat the lean solvent stream 112 to produce an enhanced solvent stream 166. According to embodiments described herein, the enhanced solvent stream 166 is a treated solvent stream that is capable of absorbing a higher concentration of acid gas than the lean solvent stream 112. The enhanced solvent stream 166 may be a highly $H_2S$-selective solvent stream that is capable of selectively absorbing a higher concentration of $H_2S$ as opposed to $CO_2$. In various embodiments, an $H_2S$ concentration of less than 4 ppm within the final sweetened gas stream 106 is achieved using the enhanced solvent stream 166.

In various embodiments, the solvent treater 164 is a chiller that is configured to produce the enhanced solvent stream 166 by cooling the lean solvent stream 112 to at least about ambient, such as about 20° C. to 25° C., or to at least about 5° C. below ambient, or to at least about 10° C. below ambient, or to at least about 20° C. below ambient, or to a temperature that is the same as, or slightly lower than, that of the partially-sweetened gas stream 120E entering the final co-current contacting system 104F. For example, the solvent treater 164 may be an ammonia chiller, a cold water flow from a cooling water tower, or any other suitable type of chiller.

Figure 2:
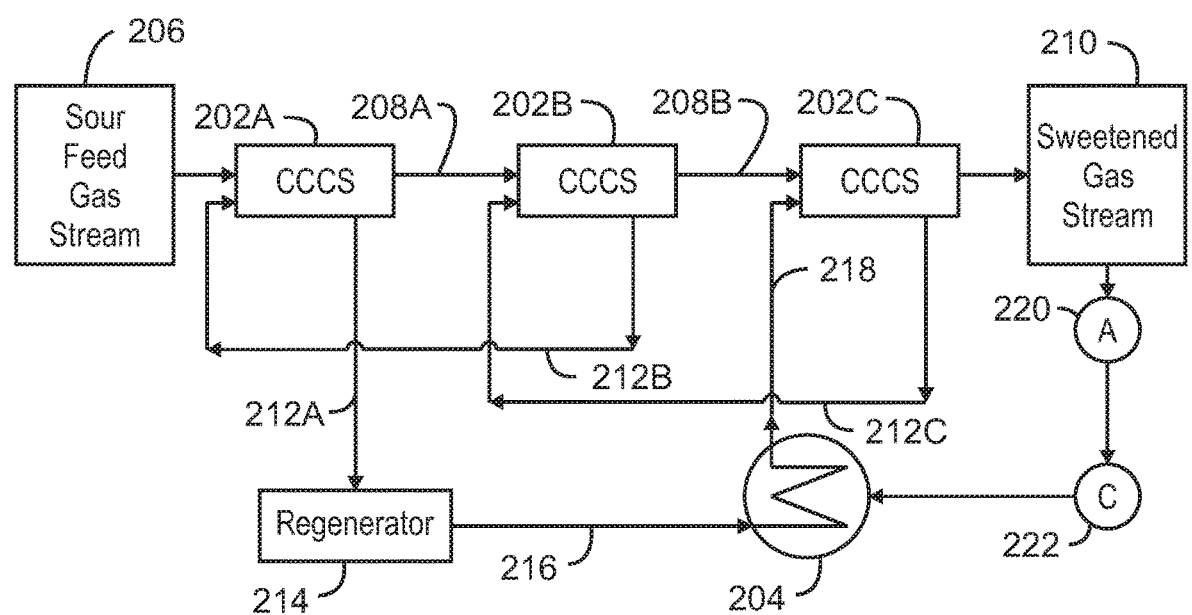
FIG. 2 is a process flow diagram of a separation system that includes a number of co-current contacting systems and a chiller for enhanced acid gas removal.

In some embodiments, an analyzer (not shown) and a controller (not shown) may be coupled to the solvent treater 164, as described in further detail with respect to FIG. 2. The analyzer may be configured to determine the acid gas concentration of the final sweetened gas stream 106 exiting the final co-current contacting system 104F. The controller may then adjust the temperature of the solvent treater 164 based on the analysis of the sweetened gas stream 106.

In some embodiments, the solvent treater 164 is an anion exchange bed that produces the enhanced solvent stream 166 by removing residual HS— and $HCO_3$— from the lean solvent stream 112. In other embodiments, the solvent treater 164 is an electrodialysis unit that is configured to produce the enhanced solvent stream 166 by reducing the lean load of the lean solvent stream 112. In these embodiments, the solvent treater 164 may also be used to remove heat stable salt contaminants from the lean solvent stream 112.

In other embodiments, the solvent treater 164 produces the enhanced solvent stream 166 by injecting an enhancement fluid into the lean solvent stream 112 that enhances the solvent's ability to selectively absorb acid gas. For example, a liquid $H_2S$ scavenger may be added to the lean solvent stream 112 to increase the solvent's ability to remove residual $H_2S$ within the partially-sweetened gas stream 120E. In some embodiments, a controlled bypass (not shown) may be used to ensure that the final sweetened gas stream 106 has a concentration of 3-4 ppm $H_2S$, not 0 ppm, which would be a waste of scavenger.

The process flow diagram of FIG. 1A is not intended to indicate that the gas processing system 100 is to include all of the components shown in FIG. 1A. Further, any number of additional components may be included within the gas processing system 100, depending on the details of the specific implementation. For example, the gas processing system 100 may include any suitable types of heaters, chillers, condensers, liquid pumps, gas compressors, blowers, bypass lines, other types of separation and/or fractionation equipment, valves, switches, controllers, and pressure-measuring devices, temperature-measuring devices, level-measuring devices, or flow-measuring devices, among others. Moreover, the gas processing system 100 may include any number of additional co-current contacting systems.

In some embodiments, the lean solvent stream 112 taken from the regenerator 110 is only directed into the final co-current contacting system 104F, not the fifth co-current contacting system 104E. In those embodiments, the entire lean solvent stream 112 is sent through the solvent treater 164 to produce the enhanced solvent stream 166.

In some embodiments, a portion of the rich solvent stream 128 is acidified before the rich solvent stream 128 enters the regenerator 110. This may be accomplished by adding 1-2 weight percent (wt. %) phosphoric acid to the rich solvent stream 128. Acidifying the rich solvent stream 128 may allow the rich solvent stream 128 to release more acid gas during the regeneration process.

Figure 1B:
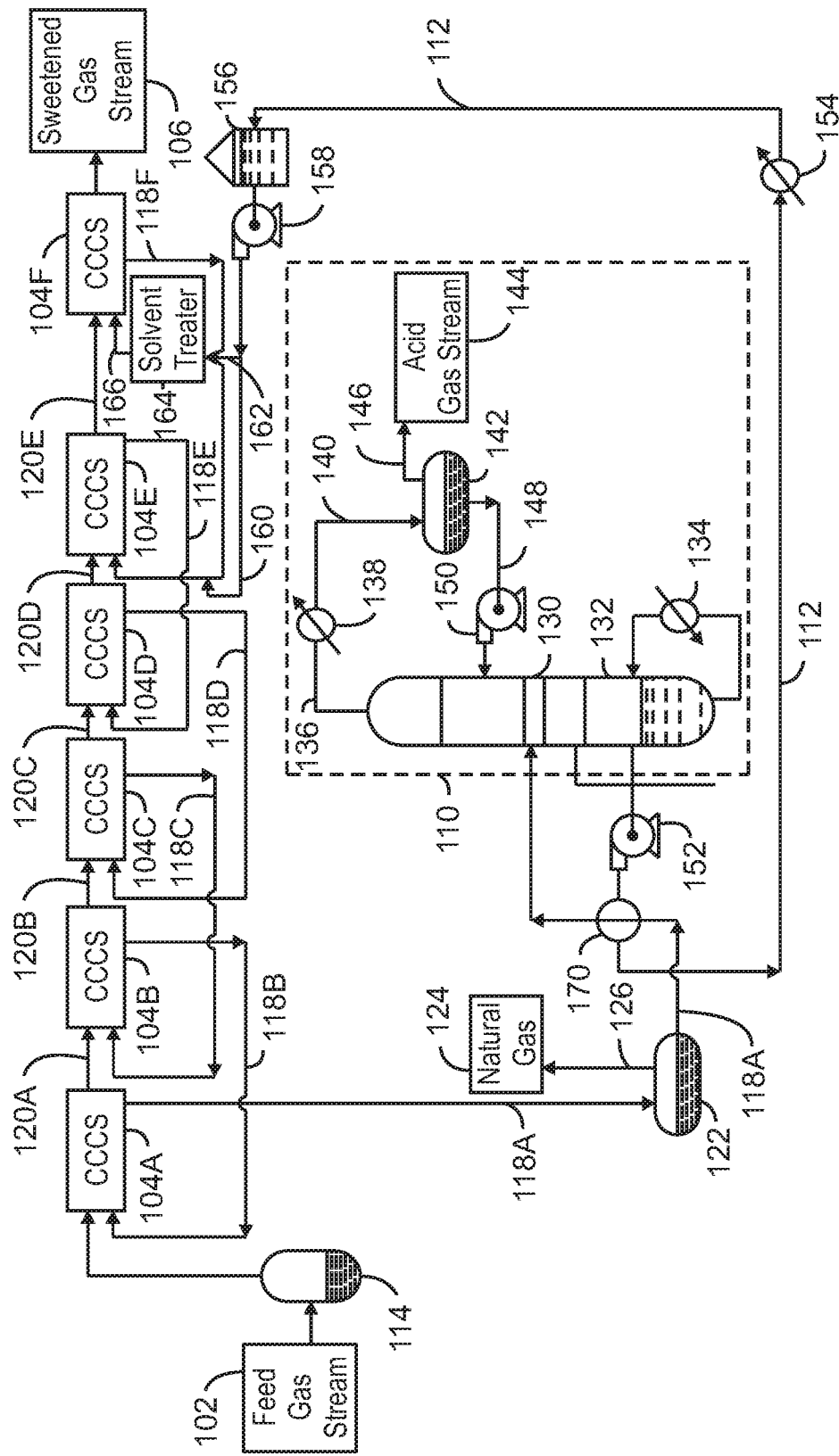
FIG. 1B is a process flow diagram of another gas processing system that includes a co-current flow scheme and is configured for enhanced acid gas removal.

FIG. 1B is a process flow diagram of another gas processing system 168 that includes a co-current flow scheme and is configured for enhanced acid gas removal. Like numbered items are as described with respect to FIG. 1A. Operation of the gas processing system 168 of FIG. 1B is similar to that of the gas processing system 100 of FIG. 1A. However, in the gas processing system 168 of FIG. 1B, the first co-current contacting system 104A receives the partially-loaded solvent stream 118B from the second co-current contacting system 104B. Therefore, the gas processing system 168 does not include the semi-lean solvent stream 108.

Because the partially-loaded solvent stream 118B received by the first co-current contacting system 104A in FIG. 1B has already been processed through the second co-current contacting system 104B, the partially-loaded solvent stream 118B received by the first co-current contacting system 104A may be very rich. For this reason, it may be desirable to provide some level of intermediate processing of the partially-loaded solvent stream 118B.

Alternatively, a semi-lean solvent stream could be taken from other sweetening operations in the gas processing system 168 and used, at least in part, as an amine solution for the first or second co-current contacting system 104A or 104B. In this respect, there are situations in which a single type of solvent is used for more than one service in the gas processing system 168. This is referred to as integrated gas treatment. For example, MDEA may be used both for high-pressure, $H_2S$-selective acid gas removal, as well as in a Claus tail gas treating (TGT) process. The rich amine stream from the TGT process is not heavily loaded with $H_2S$ and $CO_2$, owing to the low pressure of the process. Thus, in some embodiments, the rich amine stream from the TGT process is used as a semi-lean stream for the first or second co-current contacting system 104A or 104B. The semi-lean stream (not shown) may be pumped to a suitable pressure and injected into the first or second co-current contacting system 104A or 104B, possibly along with the partially-loaded solvent stream from the succeeding co-current contacting system.

Further, in the gas processing system 168 of FIG. 1B, the first partially-loaded solvent solution 118A is flowed through a heat exchanger 170 after being flowed through the flash drum 122. Within the heat exchanger 170, the temperature of the first partially-loaded solvent solution 118A is increased via heat exchange with the lean solvent stream 112 taken from the regenerator 110. This serves to heat the first partially-loaded solvent solution 118A before introduction into the regenerator 110, while cooling the lean solvent stream 112.

The process flow diagram of FIG. 1B is not intended to indicate that the gas processing system 168 is to include all of the components shown in FIG. 1B. Further, any number of additional components may be included within the gas processing system 168, depending on the details of the specific implementation. For example, the gas processing system 168 may include any suitable types of heaters, chillers, condensers, liquid pumps, gas compressors, blowers, bypass lines, other types of separation and/or fractionation equipment, valves, switches, controllers, and pressure-measuring devices, temperature-measuring devices, level-measuring devices, or flow-measuring devices, among others. Moreover, the gas processing system 168 may include any number of additional co-current contacting systems.

According to the embodiments described in FIGS. 1A and 1B, the gas processing systems 100 and 168 include a countercurrent arrangement of co-current contactors. However, it is to be understood that the embodiments described herein also apply to a parallel configuration of co-current contactors where each stage is fed with a freshly-generated solvent stream. Moreover, the individual co-current contactors may be arranged in a myriad of different configurations, including both horizontal and vertical sections, stages with or without in-line separation immediately following contacting, and with dehydration, $H_2S$ removal, and $CO_2$ removal occurring in subsequent portions of a single in-line device. In addition, all of the co-current contacting systems may be bundled into a single pressure vessel oriented vertically or horizontally.

Separation System

FIG. 2 is a process flow diagram of a separation system 200 that includes a number of co-current contacting systems 202A-C and a chiller 204 for enhanced acid gas removal. The separation system 200 may be implemented as part of a gas processing system, such as the gas processing system 100 or 168 discussed with respect to FIG. 1A or 1B. The gas processing system may utilize a number of co-current contacting systems 202A-C connected in series, such as the co-current contacting systems 104A-F discussed with respect to FIGS. 1A and 1B. In the illustrative arrangement shown in FIG. 2, a first co-current contacting system 202A, a second co-current contacting system 202B, and a third co-current contacting system 202C are provided.

A sour feed gas stream 206 may be flowed into the first co-current contacting system 202A. The first co-current contacting system 202A may generate a first partially-sweetened gas stream 208A, which may be flowed from the first co-current contacting system 202A to the second co-current contacting system 202B. The second co-current contacting system 202B may then generate a second partially-sweetened gas stream 208B, which may be flowed from the second co-current contacting system 202B to the third co-current contacting system 202C. In some embodiments, the third co-current contacting system 202C generates a final sweetened gas stream 210.

Each of the first, second, and third co-current contacting systems 202A-C also generates a respective rich solvent stream 212A-C. The third rich solvent stream 212C may be directed back to the second co-current contacting system 202B, and the second rich solvent stream 212B may be directed back to the first co-current contacting system 202A. In addition, the first rich solvent stream 212A may be returned to a regenerator 214. In some embodiments, the regenerator 214 is the same as, or similar to, the regenerator 110 discussed with respect to FIGS. 1A and 1B.

The regenerator 214 may remove absorbed acid gases and other impurities from the first rich solvent stream 212A, producing a lean solvent stream 216. The lean solvent stream 216 may then be sent through the chiller 204, which may reduce the temperature of the lean solvent stream 216 to produce an enhanced solvent stream 218. In various embodiments, the chiller 204 corresponds to the solvent treater 164 described with respect to FIGS. 1A and 1B. Further, in various embodiments, the enhanced solvent stream 218 is a solvent stream that is capable of absorbing a higher concentration of acid gas from the second partially-sweetened gas stream 208B. For example, the enhanced solvent stream 218 may be a highly $H_2S$-selective solvent stream that is capable of absorbing a higher concentration of $H_2S$ as opposed to $CO_2$.

The chiller 204 may be any suitable type of chiller that is capable of lowering the temperature of the lean solvent stream 216 to at least 10° F. below ambient, or to a temperature that is the same as, or slightly lower than, that of the second partially-sweetened gas stream 208B entering the third co-current contacting system 202C. For example, the chiller 204 may be an ammonia chiller or a cold water flow from a water tower. Moreover, in some embodiments, the chiller 204 includes a small addition system for injecting enhancement fluid into the lean solvent stream 216.

From the chiller 204, the enhanced solvent stream 218 may be flowed into the third co-current contacting system 202C. Within the third co-current contacting system 202C, the enhanced solvent stream 218 contacts the second partially-sweetened gas stream 208B and absorbs an increased amount of acid gas, such as $H_2S$, from the second partially-sweetened gas stream 208B. The resulting sweetened gas stream 210 may include a low concentration of acid gas, such as, for example, less than 4 ppm $H_2S$.

The separation system 200 may also include an analyzer 220 and a controller 222. The analyzer 220 may be configured to conduct an external analysis of the final sweetened gas stream 210 exiting the third co-current contacting system 202C to determine the acid gas concentration, such as the $H_2S$ and $CO_2$ concentrations, of the final sweetened gas stream 210. The controller 222 may then adjust the temperature of the chiller 204 based on the analysis of the sweetened gas stream 210. In some embodiments, using the analyzer 220 and the controller 222 within the separation system 200 results in energy savings because the chiller 204 may be operated at different temperatures depending on the acid gas concentration of the final sweetened gas stream 210.

The process flow diagram of FIG. 2 is not intended to indicate that the separation system 200 is to include all of the components shown in FIG. 2. Further, any number of additional components may be included within the separation system 200, depending on the details of the specific implementation. For example, any number of additional co-current contacting systems may be included within the separation system 200.

Figure 3:
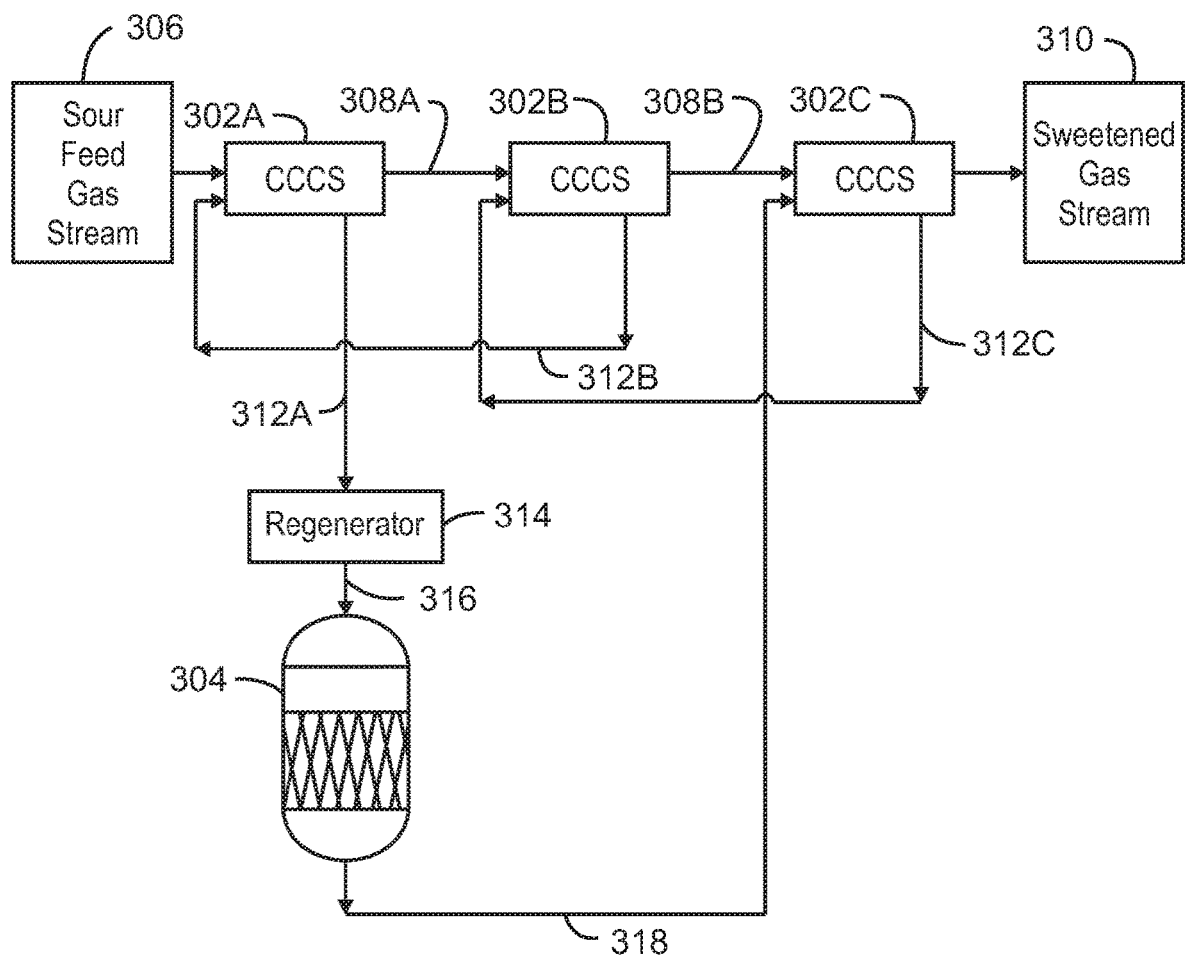
FIG. 3 is a process flow diagram of a separation system that includes a number of co-current contacting systems and an anion exchange bed for enhanced acid gas removal.

FIG. 3 is a process flow diagram of a separation system 300 that includes a number of co-current contacting systems 302A-C and an anion exchange bed 304 for enhanced acid gas removal. The separation system 300 may be implemented as part of a gas processing system, such as the gas processing system 100 or 168 discussed with respect to FIG. 1A or 1B. The gas processing system may utilize a number of co-current contacting systems 302A-C connected in series, such as the co-current contacting systems 104A-F discussed with respect to FIGS. 1A and 1B. In the illustrative arrangement shown in FIG. 3, a first co-current contacting system 302A, a second co-current contacting system 302B, and a third co-current contacting system 302C are provided.

A sour feed gas stream 306 may be flowed into the first co-current contacting system 302A. The first co-current contacting system 302A may generate a first partially-sweetened gas stream 308A, which may be flowed from the first co-current contacting system 302A to the second co-current contacting system 302B. The second co-current contacting system 302B may then generate a second partially-sweetened gas stream 308B, which may be flowed from the second co-current contacting system 302B to the third co-current contacting system 302C. In some embodiments, the third co-current contacting system 302C generates a final sweetened gas stream 310.

Each of the first, second, and third co-current contacting systems 302A-C also generates a respective rich solvent stream 312A-C. The third rich solvent stream 312C may be directed back to the second co-current contacting system 302B, and the second rich solvent stream 312B may be directed back to the first co-current contacting system 302A. In addition, the first rich solvent stream 312A may be returned to a regenerator 314. In some embodiments, the regenerator 314 is the same as, or similar to, the regenerator 110 discussed with respect to FIGS. 1A and 1B.

The regenerator 314 may remove absorbed acid gases and other impurities from the first rich solvent stream 312A, producing a lean solvent stream 316. The lean solvent stream 316 may then be sent through the anion exchange bed 304. In various embodiments, the anion exchange bed 304 corresponds to the solvent treater 164 described with respect to FIGS. 1A and 1B.

The anion exchange bed 304 may produce an enhanced solvent stream 318 by removing residual acid gases from the lean solvent stream 316. In addition, the anion exchange bed 304 may remove heat stable salt contaminants from the lean solvent stream 316.

According to embodiments described herein, the enhanced solvent stream 318 is a solvent stream that is capable of absorbing a higher concentration of acid gas from the second partially-sweetened gas stream 308B. For example, in some embodiments, the enhanced solvent stream 318 may be a highly $H_2S$-selective solvent stream that is capable of absorbing $H_2S$ more quickly than $CO_2$. In those embodiments, the anion exchange bed 304 produces the enhanced solvent stream 318 by removing residual HS— and $HCO_3$— from the lean solvent stream 316.

The process flow diagram of FIG. 3 is not intended to indicate that the separation system 300 is to include all of the components shown in FIG. 3. Further, any number of additional components may be included within the separation system 300, depending on the details of the specific implementation. For example, any number of additional co-current contacting systems may be included within the separation system 300.

Figure 4:
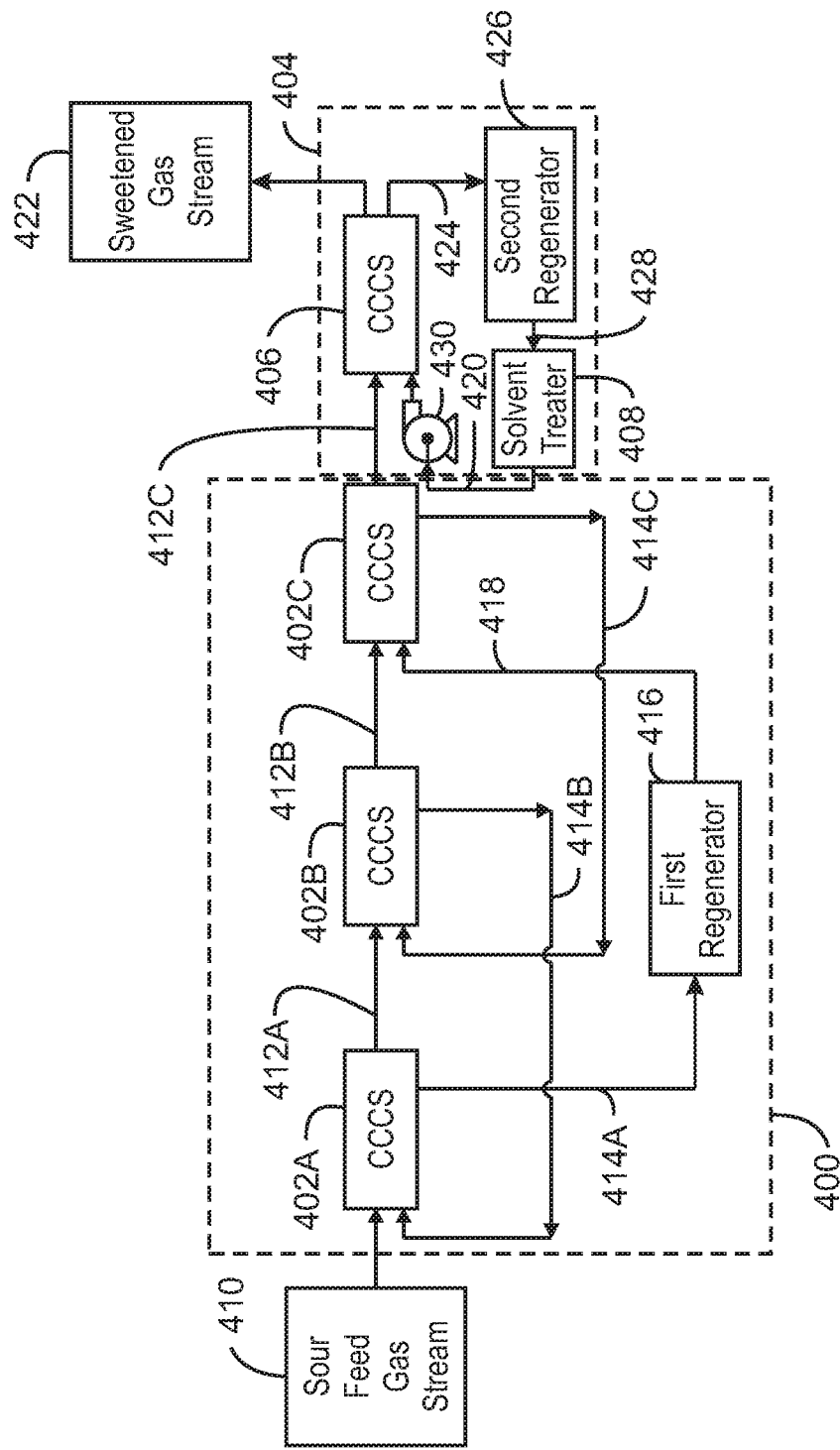
FIG. 4 is a process flow diagram of a first separation system including a number of co-current contacting systems and a second separation including a final co-current contacting system and a corresponding solvent treater.

FIG. 4 is a process flow diagram of a first separation system 400 including a number of co-current contacting systems 402A-C and a second separation system 404 including a final co-current contacting system 406 and a corresponding solvent treater 408. The first and second separation systems 400 and 404 may be implemented as part of a gas processing system, such as a gas processing system that is similar to the gas processing system 100 or 168 discussed with respect to FIG. 1A or 1B. The gas processing system may utilize a number of co-current contacting systems 402A-C and 406 connected in series, such as the co-current contacting systems 104A-F discussed with respect to FIGS. 1A and 1B. In the illustrative arrangement shown in FIG. 4, the first separation system 400 includes a first co-current contacting system 402A, a second co-current contacting system 402B, and a third co-current contacting system 402C, and the second separation system 404 includes the final co-current contacting system 406.

Within the first separation system 400, a sour feed gas stream 410 may be flowed into the first co-current contacting system 402A. The first co-current contacting system 402A may generate a first partially-sweetened gas stream 412A, which may be flowed from the first co-current contacting system 402A to the second co-current contacting system 402B. The second co-current contacting system 402B may then generate a second partially-sweetened gas stream 412B, which may be flowed from the second co-current contacting system 402B to the third co-current contacting system 402C. The third co-current contacting system 402C may then generate a third partially-sweetened gas stream 412C, which may be flowed from the second co-current contacting system 402B to the final co-current contacting system 406 within the second separation system 404.

Each of the first, second, and third co-current contacting systems 402A-C also generates a respective rich solvent stream 414A-C. The third rich solvent stream 414C may be directed back to the second co-current contacting system 402B, and the second rich solvent stream 414B may be directed back to the first co-current contacting system 402A. In addition, the first rich solvent stream 414A may be returned to a first regenerator 416. In some embodiments, the first regenerator 416 is the same as, or similar to, the regenerator 110 discussed with respect to FIGS. 1A and 1B.

The first regenerator 416 may remove absorbed acid gases and other impurities from the first rich solvent stream 414A, producing a first lean solvent stream 418. The first lean solvent stream 418 may then be recirculated into the third co-current contacting system 402C.

Within the final co-current contacting system 406, the third partially-sweetened gas stream 412C is contacted with an enhanced solvent stream 420, producing a final sweetened gas stream 422. According to embodiments described herein, the enhanced solvent stream 420 is a treated solvent stream that is capable of absorbing a high concentration of acid gas. Therefore, the final sweetened gas stream 422 may include a low concentration of acid gas, such as, for example, less than 4 ppm $H_2S$.

The final co-current contacting system 406 also generates a partially-loaded solvent stream 424. The partially-loaded solvent stream 424 may be sent to a second regenerator 426. In some embodiments, the second regenerator 426 is the same as, or similar to, the regenerator 110 discussed with respect to FIGS. 1A and 1B. The second regenerator 426 may remove absorbed acid gases and other impurities from the partially-loaded solvent stream 424, producing a second lean solvent stream 428.

According to embodiments described herein, the second lean solvent stream 428 is then sent through the solvent treater 408. The solvent treater 408 is configured to treat the second lean solvent stream 428 to produce the enhanced solvent stream 420. In various embodiments, the solvent treater 408 is the same as, or similar to, the solvent treater 164 described with respect to FIGS. 1A and 1B. The enhanced solvent stream 420 may then be sent through a pressure boosting pump 430 before being directed back into the final co-current contacting system 406.

The process flow diagram of FIG. 4 is not intended to indicate that the first and second separation systems 400 and 404 are to include all of the components shown in FIG. 4. Further, any number of additional components may be included within the first and second separation systems 400 and 404, depending on the details of the specific implementation. For example, any number of additional co-current contacting systems may be included within the first separation system 400 or the second separation system 404.

Co-Current Contacting System

Figure 5:
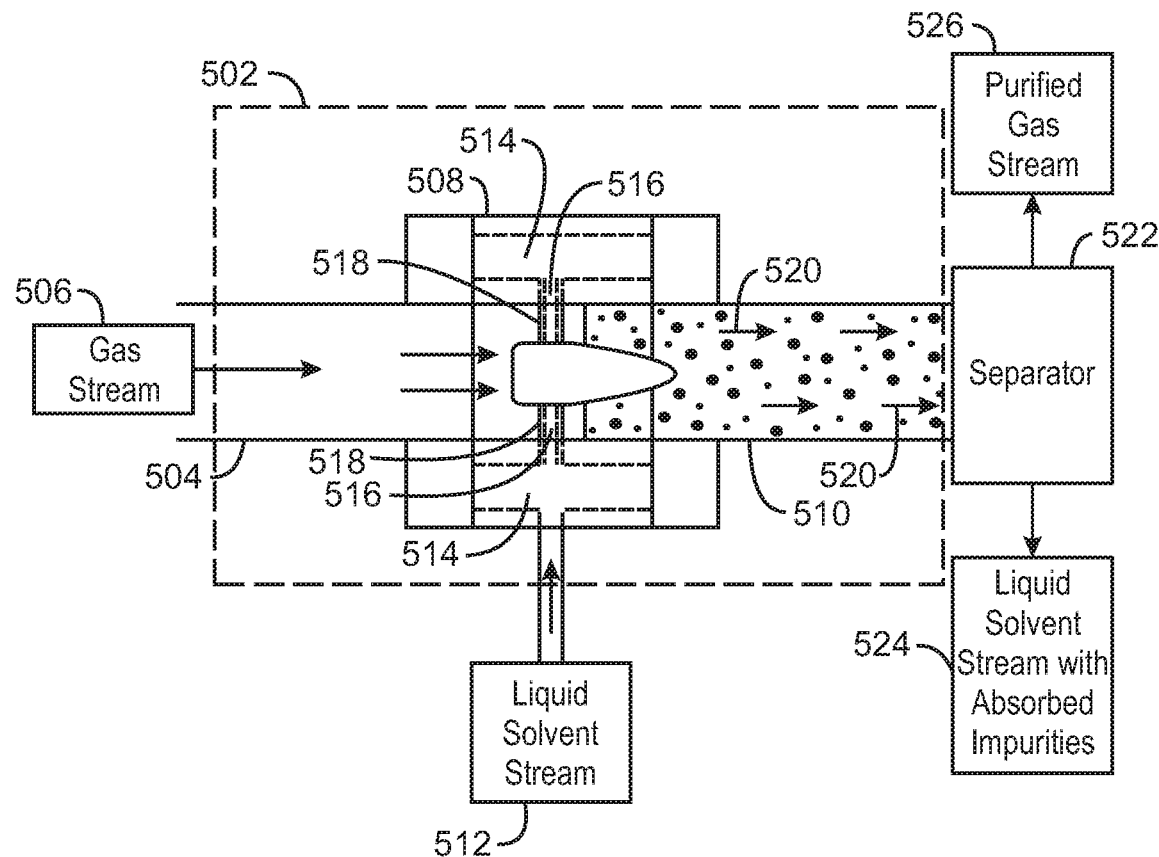
FIG. 5 is a schematic of a co-current contacting system.

FIG. 5 is a schematic of a co-current contacting system 500. The co-current contacting system 500 may provide for the separation of components within a gas stream. In addition, the co-current contacting system 500 may aid in the implementation of various gas processing systems, such as the gas processing systems 100 and 168 of FIGS. 1A and 1B, where the rapid separation of components is desired. In some embodiments, the co-current contacting system 500 is one of the co-current contacting systems 104A-F, 202A-C, 302A-C, 402A-C, and 406 discussed with respect to FIGS. 1A, 1B, 2, 3, and 4.

The co-current contacting system 500 may include a co-current contactor 502 that is positioned in-line within a pipe 504. The co-current contactor 502 may include a number of components that provide for the efficient contacting of a liquid solvent stream with a flowing gas stream 506. The liquid solvent stream can be used for the separation of impurities, such as $H_2S$ and $CO_2$, from a gas stream 506.

In various embodiments, the co-current contactor 502 includes a mixer 508 and a mass transfer section 510. As shown in FIG. 5, the gas stream 506 may be flowed through the pipe 504 and into the mixer 508. A liquid solvent stream 512 may also be flowed into the mixer 508, for example, through a hollow space 514 coupled to flow channels 516 in the mixer 508.

From the flow channels 516, the liquid solvent stream 512 is released into the gas stream 506 as fine droplets through injection orifices 518, and is then flowed into the mass transfer section 510. This may result in the generation of a treated gas stream 520 within the mass transfer section 510. The treated gas stream 520 may include small liquid droplets dispersed in a gas phase. The liquid droplets may include impurities from the gas stream 506 that were absorbed or dissolved into the liquid solvent stream 512.

The treated gas stream 520 may be flowed from the mass transfer section 510 to a separator 522, such as a cyclonic separator, a mesh screen, or a settling vessel. The separator 522 removes the liquid droplets from the gas phase. The liquid droplets may include the original liquid solvent stream with the absorbed impurities 524, and the gas phase may include a purified gas stream 526. In various embodiments, the purified gas stream 526 is a gas stream that has been purified via the removal of $H_2S$ and $CO_2$.

Method for Enhanced Acid Gas Removal within a Gas Processing System

Figure 6:
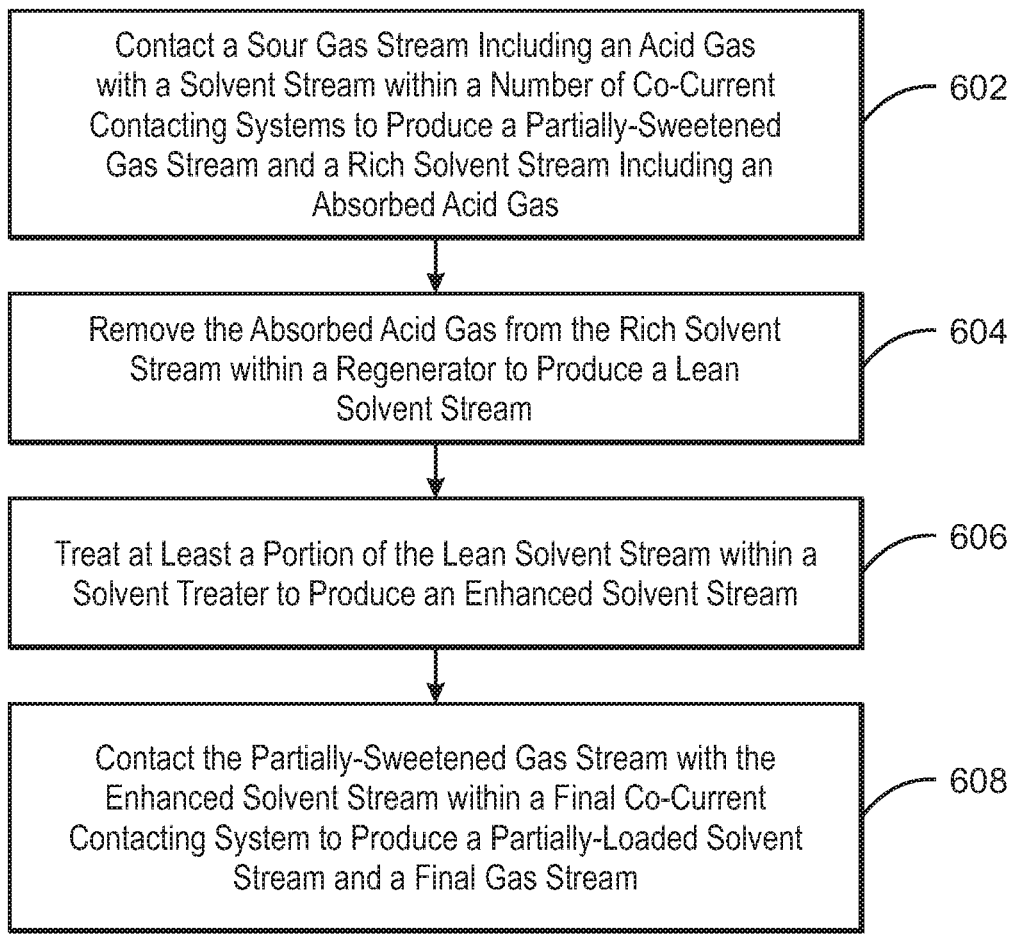
FIG. 6 is a process flow diagram showing a method for enhanced acid gas removal within a gas processing system.

FIG. 6 is a process flow diagram showing a method 600 for enhanced acid gas removal within a gas processing system. The method 600 is implemented by a gas processing system, such as the gas processing systems 100 and 168 discussed with respect to FIGS. 1A and 1B. In addition, the gas processing system may include one or more separation systems, such as the separation systems 200, 300, 400, and 404 discussed with respect to FIGS. 2, 3, and 4. Further, the gas processing system may include a number of co-current contacting systems. In various embodiments, the co-current contacting systems correspond to the co-current contacting system 500 described with respect to FIG. 5.

The method begins at block 602, at which a sour feed gas stream including an acid gas is contacted with a solvent stream within a number of co-current contacting systems to produce a partially-sweetened gas stream and a rich solvent stream including an absorbed acid gas. At least one of the co-current contacting systems is configured to send the rich solvent stream to a regenerator. In addition, in some embodiments, each of the co-current contacting systems is configured to recirculate a corresponding solvent stream to a preceding one of the co-current contacting systems.

In various embodiments, the sour feed gas stream is a sour natural gas stream. Moreover, in various embodiments, the sour feed gas stream includes at least 1,000 ppm $H_2S$. In those embodiments, the absorbed acid gas is primarily $H_2S$, and the partially-sweetened gas stream is a gas stream that has had a portion of the $H_2S$ removed.

At block 604, the absorbed acid gas is removed from the rich solvent stream within the regenerator to produce a lean solvent stream. In some embodiments, the regenerator may correspond to the regenerator 110 described with respect to FIGS. 1A and 1B.

At block 606, at least a portion of the lean solvent stream is treated within a solvent treater to produce an enhanced solvent stream. The solvent treater may correspond to the solvent treater 164 described with respect to FIGS. 1A and 1B. In some embodiments, the solvent treater is a chiller that produces the enhanced solvent stream by reducing the temperature of the lean solvent stream. In other embodiments, the solvent treater is an anion exchange bed that produces the enhanced solvent stream by removing residual HS—, $HCO_3$—, and heat stable salt contaminants from the lean solvent stream. In other embodiments, the solvent treater is an electrodialysis unit that produces the enhanced solvent stream by reducing the lean load of the lean solvent stream and removing heat stable salt contaminants from the lean solvent stream. Further, in other embodiments, the solvent treater produces the enhanced solvent stream by injecting an enhancement fluid into the lean solvent stream that increases its ability to absorb acid gas.

At block 608, the partially-sweetened gas stream is contacted with the enhanced solvent stream within a final co-current contacting system to produce a partially-loaded solvent stream and a final gas stream. In various embodiments, the final gas stream includes concentrations of less than 4 ppm $H_2S$ and less than 2-3 vol. % $CO_2$.

The process flow diagram of FIG. 6 is not intended to indicate that the steps of the method 600 are to be executed in any particular order, or that all of the steps of the method 600 are to be included in every case. Further, any number of additional steps not shown in FIG. 6 may be included within the method 600, depending on the details of the specific implementation. For example, in embodiments in which the solvent treater is a chiller, the method 600 may also include determining an acid gas concentration of the final gas stream using an analyzer, and then increasing or decreasing the temperature of the chiller based on the acid gas concentration of the final gas stream using a controller.

In some embodiments, the method 600 is implemented using two separate separation systems, such as the first and second separation systems 400 and 404 described with respect to FIG. 4. In those embodiments, the final co-current contacting system may employ intra-stage recycling of its own solvent stream using a separate regenerator. Specifically, the partially-loaded solvent stream exiting the final co-current contacting system may be sent to the regenerator, which may produce a lean solvent stream. The lean solvent stream may then be sent through the solvent treater, which may produce the enhanced solvent stream. The enhanced solvent stream may then be recirculated through the final co-current contacting system to produce the final gas stream.

While the present techniques may be susceptible to various modifications and alternative forms, the embodiments discussed above have been shown only by way of example. However, it should again be understood that the techniques are not intended to be limited to the particular embodiments disclosed herein. Indeed, the present techniques include all alternatives, modifications, and equivalents falling within the true spirit and scope of the appended claims.

What is claimed is:

1. A method for enhanced acid gas removal within a gas processing system, comprising:
    contacting a sour feed gas stream comprising an acid gas with a solvent stream within a plurality of co-current contacting systems to produce a partially-sweetened gas stream and a rich solvent stream comprising an absorbed acid gas;
    removing the absorbed acid gas from the rich solvent stream within a regenerator to produce a lean solvent stream;
    dividing the lean solvent stream into a first portion and a second portion;
    combining the first portion of the lean solvent stream with a partially-loaded solvent stream from a final co-current contacting system;
    treating the second portion of the lean solvent stream within a solvent treater to produce an enhanced solvent stream; and
    contacting the partially-sweetened gas stream with the enhanced solvent stream within the final co-current contacting system to produce the partially-loaded solvent stream and a final gas stream.

2. The method of claim 1, comprising:
    recirculating a corresponding solvent stream from each of the plurality of co-current contacting systems to a preceding one of the plurality of co-current contacting systems; and
    recirculating the partially-loaded solvent stream from the final co-current contacting system and the first portion of the lean solvent stream to a preceding one of the plurality of co-current contacting systems.

3. The method of claim 1, wherein the solvent treater comprises a chiller configured to reduce a temperature of the second portion of the lean solvent stream to at least about 5° C. below ambient temperature to produce the enhanced solvent stream.

4. The method of claim 3, comprising:
analyzing the final gas stream to determine an acid gas concentration of the final gas stream; and
increasing or decreasing a temperature of the chiller based on the acid gas concentration of the final gas stream.

5. The method of claim 1, wherein contacting the sour feed gas stream with the solvent stream within the plurality of co-current contacting systems comprises:
flowing the solvent stream into a co-current contactor via a mixer through flow channels;
flowing the sour feed gas stream into the co-current contactor via a mixer;
contacting the sour feed gas stream with the solvent stream to provide for incorporation of liquid droplets formed from the solvent stream into the sour feed gas stream; and
separating the liquid droplets from the sour feed gas stream within a separator.

6. The method of claim 1, wherein treating the second portion of the lean solvent stream within the solvent treater comprises injecting an enhancement fluid into the second portion of the lean solvent stream to produce the enhanced solvent stream, wherein the enhancement fluid is different than the solvent and capable of enhancing the ability of the solvent to selectively absorb acid gas.

7. The method of claim 6, wherein the enhancement fluid is a liquid $H_2S$ scavenger.

* * * * *